(12) United States Patent
Jung et al.

(10) Patent No.: US 9,606,095 B2
(45) Date of Patent: Mar. 28, 2017

(54) METHOD OF PREPARING GRAPHENE NANORIBBON ARRAYS AND SENSOR COMPRISING THE SAME

(71) Applicant: GWANGJU INSTITUTE OF SCIENCE AND TECHNOLOGY, Gwangju (KR)

(72) Inventors: Gun-young Jung, Gwangju (KR); yusin Pak, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 122 days.

(21) Appl. No.: 14/585,750

(22) Filed: Dec. 30, 2014

(65) Prior Publication Data

US 2015/0362470 A1  Dec. 17, 2015

(30) Foreign Application Priority Data

Jun. 11, 2014 (KR) ........................ 10-2014-0070750

(51) Int. Cl.
*G01N 33/00* (2006.01)
*C01B 31/02* (2006.01)
(52) U.S. Cl.
CPC ......... *G01N 33/0036* (2013.01); *C01B 31/02* (2013.01)
(58) Field of Classification Search
None
See application file for complete search history.

(56) References Cited

U.S. PATENT DOCUMENTS

| | | | | |
|---|---|---|---|---|
| 8,637,346 B1* | 1/2014 | Jung | ................... | H01L 21/2815 438/99 |
| 2010/0035186 A1* | 2/2010 | Hong | ...................... | H01B 1/24 430/311 |
| 2011/0253969 A1* | 10/2011 | Dai | ........................ | B82Y 30/00 257/9 |
| 2012/0085991 A1* | 4/2012 | Cohen | .................... | B82Y 10/00 257/28 |
| 2012/0261643 A1* | 10/2012 | Cohen | .................... | B82Y 10/00 257/27 |
| 2012/0294793 A1* | 11/2012 | Chen | ...................... | B82Y 30/00 423/448 |
| 2012/0301953 A1* | 11/2012 | Duan | ..................... | B82Y 30/00 435/287.9 |
| 2013/0309462 A1 | 11/2013 | Yager et al. | | |
| 2013/0309776 A1* | 11/2013 | Drndic | .................. | G01N 27/26 436/94 |
| 2013/0330523 A1* | 12/2013 | Zhang | ................ | C01B 31/0213 428/195.1 |
| 2014/0051229 A1* | 2/2014 | Dimitrakopoulos | ... | B82Y 10/00 438/458 |
| 2014/0220773 A1* | 8/2014 | Tour | ................... | C01B 31/0438 438/610 |

(Continued)

FOREIGN PATENT DOCUMENTS

JP  2013056796 A  3/2013
KR  1020110133452 A  12/2011

*Primary Examiner* — Andre Allen
(74) *Attorney, Agent, or Firm* — Hauptman Ham, LLP (57) ABSTRACT

Disclosed herein are a method of manufacturing large area graphene nanoribbons, which have no residual layer by interposing a chromium layer between a resist layer and a graphene layer, and a sensor including the graphene nanoribbons.

11 Claims, 5 Drawing Sheets

(56) References Cited

U.S. PATENT DOCUMENTS

| | | | |
|---|---|---|---|
| 2015/0108499 A1* | 4/2015 | Alptekin | H01L 21/0237 257/77 |
| 2015/0123078 A1* | 5/2015 | Seo | H01L 29/1606 257/29 |
| 2016/0056240 A1* | 2/2016 | Yamaguchi | H01L 29/66742 257/29 |

* cited by examiner

METHOD OF PREPARING GRAPHENE NANORIBBON ARRAYS AND SENSOR COMPRISING THE SAME

CROSS REFERENCE TO RELATED APPLICATION

This application claims the benefit of Korean Patent Application No. 10-2014-0070750, filed on Jun. 11, 2014, entitled "METHOD OF PREPARING GRAPHENE NANORIBBON ARRAYS AND SENSOR COMPRISING THE SAME", which is hereby incorporated by reference in its entirety into this application.

BACKGROUND

1. Technical Field

The present invention relates to a method of preparing graphene nanoribbons and a sensor including the same. More particularly, the present invention relates to a method of manufacturing large-area graphene nanoribbons having no residual layer by interposing a chromium layer between a resist layer and a graphene layer, and a sensor including the same.

2. Description of the Related Art

Hydrogen is a future energy source widely utilized in industry and academia. However, hydrogen is colorless and odorless and has high ignitability, and thus requires safe handling. Thus, there has been demand for studies on a sensor as a safeguard. Although earlier studies were focused on metal oxide-based sensors, these sensors could operate at a high temperature of 400° C. or higher. Accordingly, studies on sensors based on rare earth metals such as palladium or platinum have been conducted. Although the rare earth metal-based sensors can operate at room temperature, the sensors have a thick structure when prepared using original bulk materials, and thus exhibit poor properties in terms of sensitivity and response speed. Thus, researchers sought to utilize nanostructured palladium or platinum, which led to development of 1D palladium or platinum nanowire sensors having a considerable potential in terms of sensitivity and response speed. Nowadays, researchers' attention is focused on use of 0D nanoparticles. In this case, there is a need for a new material capable of providing a wide and stable area in which the nanoparticles can be electrically connected to one another and well dispersed. For this purpose, graphene, which has recently been developed, are considered as a proper material.

However, when typical CVD graphene or graphene oxides grown via chemical vapor deposition (CVD) allowing a large-area processing are used as a base layer for rare earth metals, there is a problem of reduction in response speed. Thus, there is demand for small graphene. In addition, from the viewpoint of sensor applications, it is required that nanostructures be regularly distributed in an aligned manner and that graphene have no foreign materials left on surfaces thereof, which otherwise could disturb hydrogen sensing reaction of rare earth metals. Thus, there is a need for fine pattering using lithography.

However, despite using any existing lithography techniques for graphene patterning, there is still a problem in that photoresists having been used in patterning remain in a thick layer on surfaces of graphene. That is to say, in graphene patterning with lithography, photoresists have to be spin-coated directly onto the surfaces of graphene, and thus there is actually no way to easily remove photoresist after a lithography process. Although heat treatment at high temperature has been employed to remove photoresists, this process can cause defects in graphene and is time consuming and expensive.

REFERENCE LITERATURES

1. Korean Patent Publication No. 10-2011-133452
2. US Patent Publication No. 2013-309562
3. Japanese Patent Laid-Open Publication No. 2013-56796

BRIEF SUMMARY

It is one aspect of the present invention to provide graphene nanoribbons which have no residual layer and have various regularities and line widths.

It is another aspect of the present invention to provide a sensor which exhibits good properties in terms of sensitivity, response speed, repeatability, and stability.

In accordance with one aspect of the present invention, a method of preparing graphene nanoribbons includes: sequentially forming a chromium layer and a resist layer on a graphene layer; and forming a pattern on the resist layer and the chromium layer, followed by forming a graphene pattern using the pattern as a mask.

The method may include: sequentially forming a chromium layer and a resist layer on a graphene layer; forming a chromium pattern using the resist layer as a mask; and etching the graphene layer using the chromium pattern as a mask.

The method may include: sequentially forming a chromium layer and a resist layer on a graphene layer; forming a resist pattern on the resist layer; forming a chromium pattern by etching the chromium layer using the resist pattern as a mask; removing the resist pattern; forming a graphene pattern by etching the graphene layer using the chromium pattern as a mask; and removing the chromium pattern.

In accordance with another aspect of the present invention, a sensor including the graphene nanoribbons prepared by the method is provided.

BRIEF DESCRIPTION OF THE DRAWINGS

The above and other aspects, features, and advantages of the present invention will become apparent from the detailed description of the following embodiments in conjunction with the accompanying drawings, in which.

DETAILED DESCRIPTION

Hereinafter, exemplary embodiments of the present invention will be described in detail with reference to the accompanying drawings. It should be understood that the present invention is not limited to the following embodiments and may be embodied in different ways, and that all equivalents and substitutes falling within the spirit and scope of the present invention as defined by the appended claims are intended to be encompassed thereby.

It will be understood that when an element such as a layer, film, region or substrate is referred to as being placed "above" or "on" another element, it can be directly placed on the other element, or intervening layer(s) may also be present. In addition, as used herein, directional expressions such as upward, upper (portion), an upper surface, etc. may also be understood as the meanings of downward, lower (portion), a lower surface, etc. In other words, expressions of spatial directions should be understood as relative directions, but should not be limitedly understood as denoting absolute directions.

In the drawings, thicknesses of various layers and regions are enlarged or omitted for clarity. Like components will be denoted by like reference numerals throughout the specification.

Hereinafter, embodiments of the present invention will be described in detail with reference to the accompanying drawings.

Figure 1:
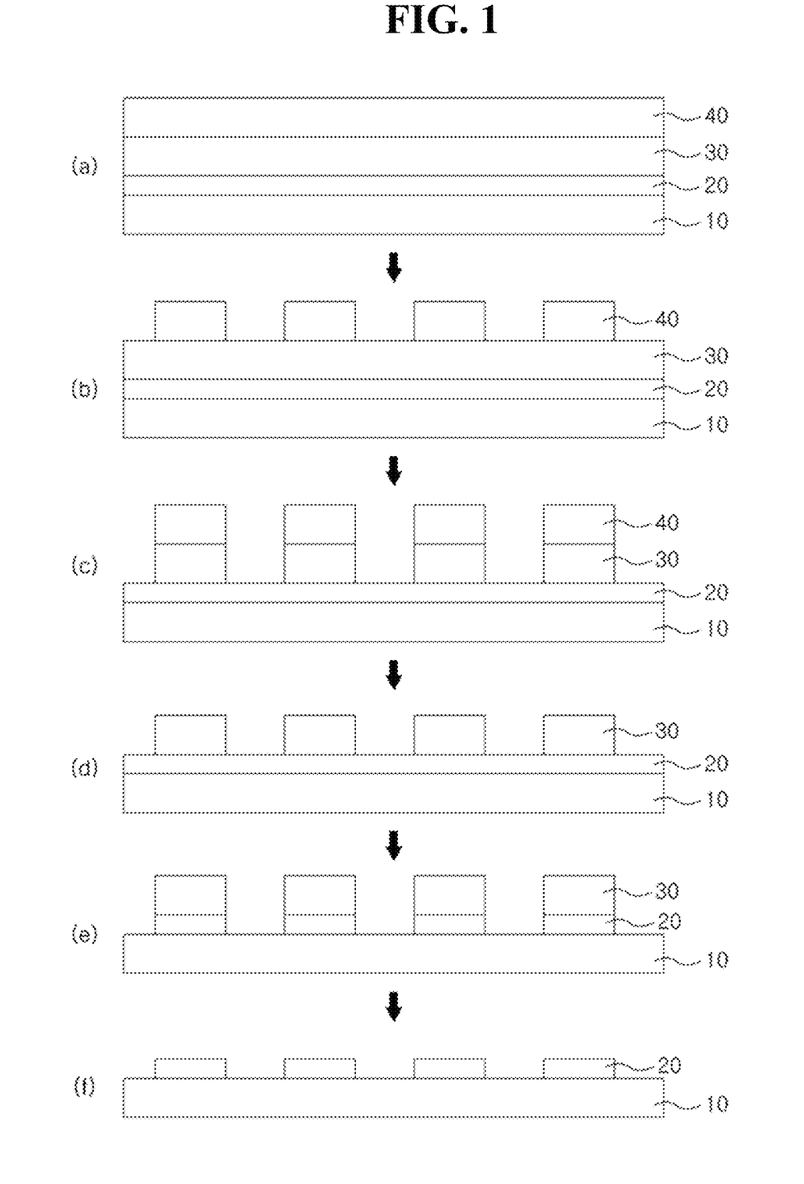
FIG. 1 shows a method of preparing graphene nanoribbons according to the present invention.

FIG. 1 shows a method of preparing graphene nanoribbons according to the present invention. Referring to FIG. 1, the method includes: sequentially forming a chromium layer and a resist layer on a graphene layer; and forming a pattern on the resist layer and the chromium layer, followed by forming a graphene pattern using the pattern as a mask.

Referring to FIG. 1, a substrate 10 having a graphene layer 20 formed thereon is provided. By way of example, the substrate 10 may include a Si substrate having a $SiO_2$ layer.

The graphene layer 20 may be formed on the substrate 10 by various methods. By way of example, the graphene layer 20 may be formed by transfer of graphene to the substrate 10, wherein the graphene have been grown via CVD on a catalyst layer.

Transferring may be accomplished by etching the catalyst layer using polydimethylsiloxane (PDMS) or polymethylmethacrylate (PMMA) as a support layer.

A chromium layer 30 and a resist layer 40 are sequentially formed on the graphene layer 20. By way of example, the chromium layer 30 may be formed by electron-beam evaporation, sputtering, physical vapor deposition (PVD), or the like. For example, the chromium layer may be formed using an e-beam coater, without being limited thereto.

The chromium layer 30 may have a thickness of 10 nm to several micrometers, preferably 10 nm to 5 μm, more preferably 10 nm to 20 nm.

The resist layer 40 may be formed by, for example, spin coating, without being limited thereto.

The resist layer 40 may be formed of UV-curable materials. The resist layer 40 may contain polymer materials. By way of example, the resist layer 40 may be an SU-8 layer or a polydimethylsiloxane (PDMS) layer. For example, the resist layer 40 may have a thickness of 400 nm to 500 nm.

The method includes forming a nanoscale-wide chromium pattern. Formation of the nanoscale-wide chromium pattern includes forming a resist pattern (Step 1b) and transferring the resist pattern to the chromium layer 30 (Step 1c).

Referring to FIG. 1, the resist pattern may be formed by any method known in the art without limitation. For example, selective etching using nanopatterning techniques may be employed. For this selective etching, mask patterning methods, such as laser interference lithography, electron-beam lithography, focused ion beam (FIB) lithography, nano-imprinting, mask formation using $SiO_2$ nanoparticles, self-assembled metal mask, and the like, may be employed.

In the present invention, laser interference lithography which allows a large area resist pattern to be realized at low cost within a short period of time may be used. Laser interference lithography is a technology wherein a substrate coated with a photo-curable material (photoresist) is irradiated with interference fringes generated in the overlap region of light beams using a high-coherent light source such as a laser, thereby exposing a predetermined pattern on the photoresist according to an intensity distribution of the interference fringes. In the method as set forth above, after exposure of the resist pattern, residual resists may be removed by dry etching, such as reactive ion etching (RIE), inductively coupled plasma reactive ion etching (ICP-RIE), chemically assisted ion beam etching (CAIBE), and the like.

In the present invention, a chromium pattern may be formed by transfer of the resist pattern to the chromium layer (Step 1c). In other words, the chromium layer may be subjected to wet etching using the resist pattern as a mask. In wet etching, any solution for chromium etching known in the art may be used.

In the present invention, a graphene pattern may be formed by etching the graphene layer using the chromium pattern as a mask. Although the graphene layer may be subjected to etching without removing the resist pattern on the chromium layer, the graphene layer is preferably subjected to etching (Step 1e) subsequent to removal of the resist pattern (Step 1d). The resist pattern or graphene may be removed by dry etching or $O_2$ plasma etching. In addition, the chromium pattern may be removed using the solution for chromium etching, thereby obtaining a nanoscale graphene pattern. The chromium pattern and the graphene pattern may have a width of 100 nm to several microns, preferably 100 nm to 5 μm, more preferably 100 nm to 200 nm.

In the present invention, the chromium pattern is used as a mask to form the graphene pattern. The chromium pattern may be transferred from the resist pattern and formed to a nanoscale width by wet etching. On the contrary, a platinum or aluminum layer has a problem in that the layer is likely to be removed together with graphene due to low adhesion thereof during developing. In addition, a gold or nickel layer has difficulty in forming a pattern due to rapid penetration of an etching solution into the layer.

In the present invention, the problem that resists remain on graphene can be solved by interposing the chromium layer between the graphene layer and the resist layer.

In accordance with another aspect of the present invention, there is provided a sensor including graphene nanoribbons prepared by the method as set forth above.

The sensor may be formed by various methods. For example, the sensor may be formed by forming a catalyst layer on the graphene nanoribbons prepared by the method and partially forming electrodes in the catalyst layer.

For example, the catalyst layer may be formed of palladium or platinum.

The sensor including the graphene nanoribbons prepared by the method according to the invention can have enhanced accuracy due to absence of foreign materials such as resists on surfaces of graphene. Moreover, the sensor can exhibit good properties in terms of sensitivity, response speed, repeatability, and stability, since the graphene ribbons having nanoscale thickness and width can be used a base layer of the sensor.

According to the present invention, the problem of having a residual layer can be solved by interposing one simple metal layer between graphene and photoresists. In the present invention, there is proposed a chromium layer as the metal layer, which allows nanoscale pattern transfer by wet etching unlike most metals. Through the inventors' studies, it has been found that at least 100 nm to 200 nm scale patterns could be transferred, and thus the present invention can also be applied to various fields other than manufacture of graphene nanoribbons. Particularly, when combined with the advantage of laser interference lithography realizing regular large-area nanostructures in an inexpensive, rapid process, the present invention can provide significant synergistic effects. In particular, the method according to the present invention is considerably simple as compared with a conventional metal pattern manufacturing process which includes, after patterning, deposition of a metal layer and lift-off of used photoresists with organic materials.

The sensor including the graphene nanoribbons prepared by the method according to the invention can have enhanced accuracy due to absence of foreign materials such as resists on surfaces of graphene. Moreover, the sensor can exhibit good properties in terms of sensitivity, response speed, repeatability, and stability, in that the graphene ribbons having nanoscale thickness and width can be used a base layer of the sensor.

Next, the present invention will be described in more detail with reference to examples. However, it should be noted that these examples are provided for illustration only and should not be construed in any way as limiting the invention.

EXAMPLE 1

For growth of graphene, a Cu/Ni thin film was formed on a $SiO_2/Si$ substrate (thickness of $SiO_2$: 300 nm) by electron-beam evaporation, followed by loading the substrate into an ICP-CVD chamber. The substrate was heated from room temperature to 650° C. at an initial pressure of $5 \times 10^{-7}$ Ton. The substrate was cleaned using an RF plasma source in a hydrogen atmosphere, followed by growing graphene on the substrate at 100 W plasma power for 3 minutes using an $Ar/C_2H_2$ mixed gas. After cooling, the graphene grown on the substrate was transferred to another $SiO_2/Si$ substrate (thickness of $SiO_2$: 300 nm), thereby forming a graphene sheet on the $SiO_2/Si$ substrate.

Chromium was deposited to a thickness of 10 nm on the graphene sheet sample by electron-beam evaporation. Next, AZ GXR 601, as a photoresist, was spin-coated onto chromium, followed by heat treatment at 115° C. for 1 minute. Then, the sample was exposed to 32 $mJ/cm^2$ irradiation using a laser interference lithography apparatus ($\lambda$=325 nm). After exposure, the sample was subjected to etching in MIF 300 solution for 40 seconds, followed by drying and heat treatment. A residual layer was removed by oxygen plasma etching (20 W, 50 sccm) for 30 seconds. The sample was dipped into a chromium etching solution (CR-75) for 40 seconds, followed by washing with distilled water. Next, in order to form a graphene pattern, oxygen RIE (100 W, 50 sccm) was performed for 100 seconds. The sample was dipped again into a chromium etching solution (CR-75) to remove the chromium pattern, followed by washing with distilled water.

COMPARATIVE EXAMPLE 1

In comparative Example 1, a chromium layer was not interposed between graphene and a resist layer. In other words, after spin coating resists onto a graphene layer, the graphene layer was subjected to etching with oxygen plasma, followed by removing the resists, thereby obtaining graphene nanoribbons.

Figure 2:
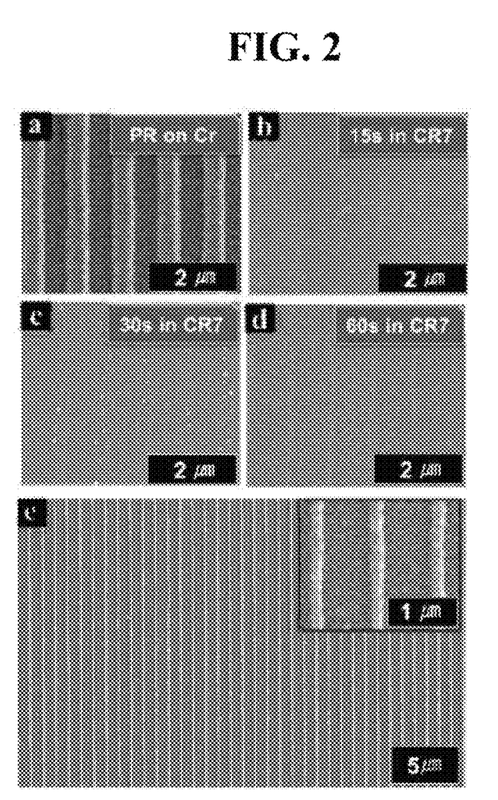
FIG. 2 is SEM images showing that a chromium pattern was transferred to graphene and formed on the graphene.

FIG. 2 is SEM images showing that a chromium pattern was transferred to graphene and formed on the graphene. FIG. 2a is an image before removal of a resist pattern on chromium, and FIGS. 2b to 2d are SEM images after dipping into a chromium etching solution. It can be seen that etching of chromium is proceeding in view of the fact that the pattern becomes narrower over time. FIG. 2e is an SEM image after CF4 plasma treatment of the sample of FIG. 2d. Referring to FIG. 2d, it can be seen that regular chromium patterns are formed in series.

Figure 3:
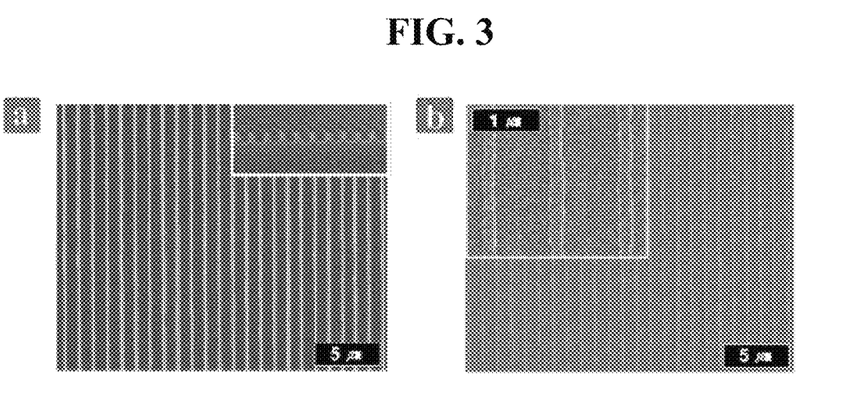
FIG. 3 is images of regularly arranged photoresist and chromium patterns, respectively.

FIG. 3a is an SEM image of photoresist patterns (AZ GXR 601) having a height of 500 nm regularly arranged at a pitch of 1 μm with a 800 nm gap therebetween (after Step 1b). FIG. 3b is an image of chromium patterns after Step 1d (after etching with RC-75 for 50 seconds). FIG. 3b shows that the photoresist patterns have been well transferred to a chromium layer having a thickness of 10 nm. Comparing FIG. 3a with FIG. 3b, while the width of the chromium pattern is similar to that of the photoresist pattern, the pattern in FIG. 3b has rougher edges than the pattern in FIG. 3a, due to the characteristics of wet etching.

Figure 4:
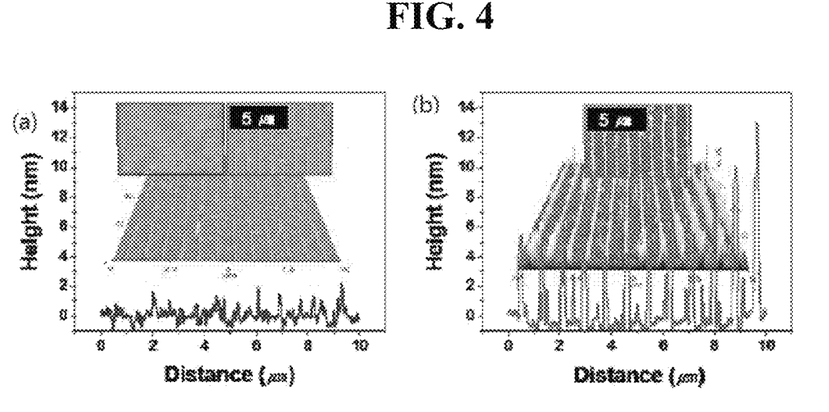
FIG. 4 is AFM images of graphene nanoribbons prepared in Example 1 and Comparative Example 1.

FIG. 4 is AFM images of the graphene nanoribbons prepared in Example 1 (FIG. 4a) and Comparative Example 1 (FIG. 4b). The image on the left of FIG. 4a shows the graphene sheet formed by CVD, and the images on the right and in the middle of FIG. 4a represent the graphene nanoribbons prepared in Example 1. Comparing FIGS. 4a with FIG. 4b, it can be seen that the graphene nanoribbons of Example 1 have almost the same bottom color as compared with the graphene sheet manufactured by CVD, and that the graphene nanoribbons of Example 1 have no foreign materials having a height of 1 nm or higher on surfaces thereof. A surface profile of FIG. 4a shows that no resist residues are present. In addition, it can be seen that the width of the nanoribbon is almost the same as that of the resist. In comparison, it is confirmed that, in Comparative Example 1 (FIG. 4b), a large amount of residue is present at an average height of about 4 nm.

Figure 5:
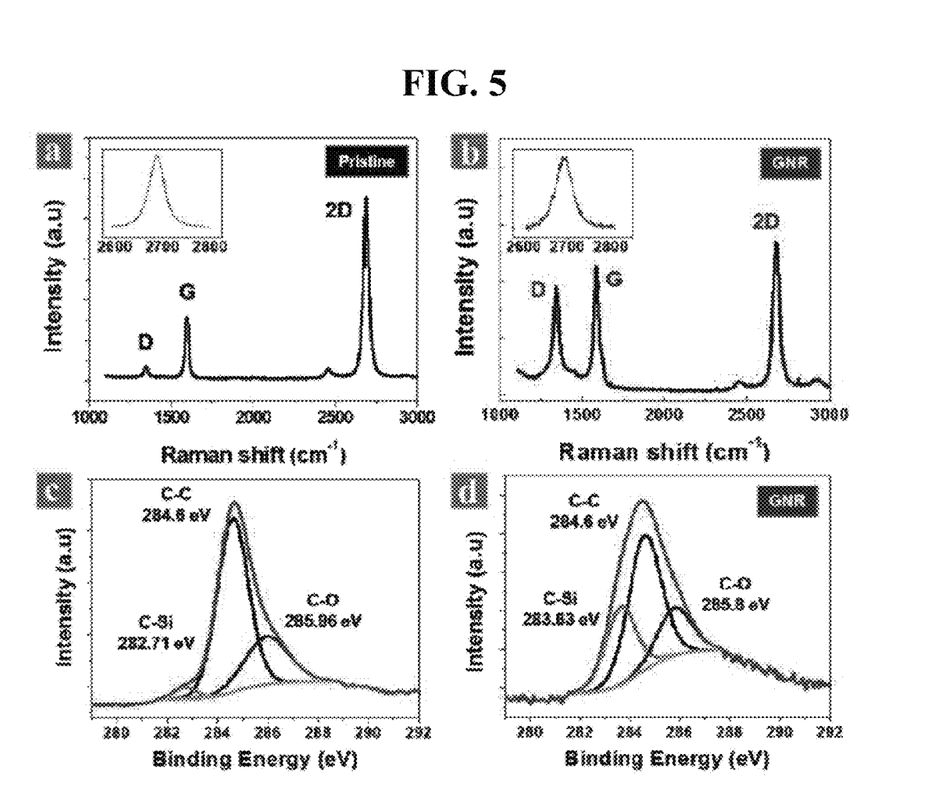
FIG. 5 is graphs depicting results obtained by investigating the pattern of Example 1 using a micro Raman spectroscope and an X-ray spectroscope.

FIG. 5 shows results obtained by investigating the pattern of Example 1 using a micro Raman spectroscope and an X-ray spectroscope. FIG. 5a is a Raman spectrum of the graphene sheet manufactured by CVD, and FIG. 5b is a Raman spectrum of Example 1.

Since, in both FIG. 5a and FIG. 5b, a 2D peak corresponds to a single component Lorentizian function, the graphene nanoribbons of Example 1 retain graphene characteristics even after patterning thereof. In addition, since a considerable increase in D peak in FIG. 5b results from the fact that graphene was cut during etching to produce numerous dangling bonds (edges), the presence of graphene nanoribbons can be expected.

In FIG. 5c and FIG. 5d, there is not much change in C—O peak. This shows that the graphene nanoribbons of Example 1 did not suffer from significant oxidation sufficient to cause change in graphene characteristics throughout patterning thereof

EXAMPLE 2

For manufacture of a sensor, the graphene nanoribbons prepared in Example 1 were coated with a 2 nm thick palladium electrode and a 90 nm thick gold electrode by electron-beam evaporation. The electrodes were spaced apart 50 μm from each other and had a length of 5000 μm.

COMPARATIVE EXAMPLE 2

The graphene sheet prepared by CVD was coated with a 2 nm thick palladium electrode and a 90 nm thick gold electrode by electron-beam evaporation.

A hydrogen detection test was conducted under the same conditions (30% humidity, 0.01 V), while varying a hydrogen concentration and a pattern width of the graphene nanoribbons. 99.999% of hydrogen was supplied at a flow rate of 1800 sccm for 15 minutes, given varying hydrogen concentrations (1000 ppm, 500 ppm, 100 ppm, 30 ppm).

Figure 6:
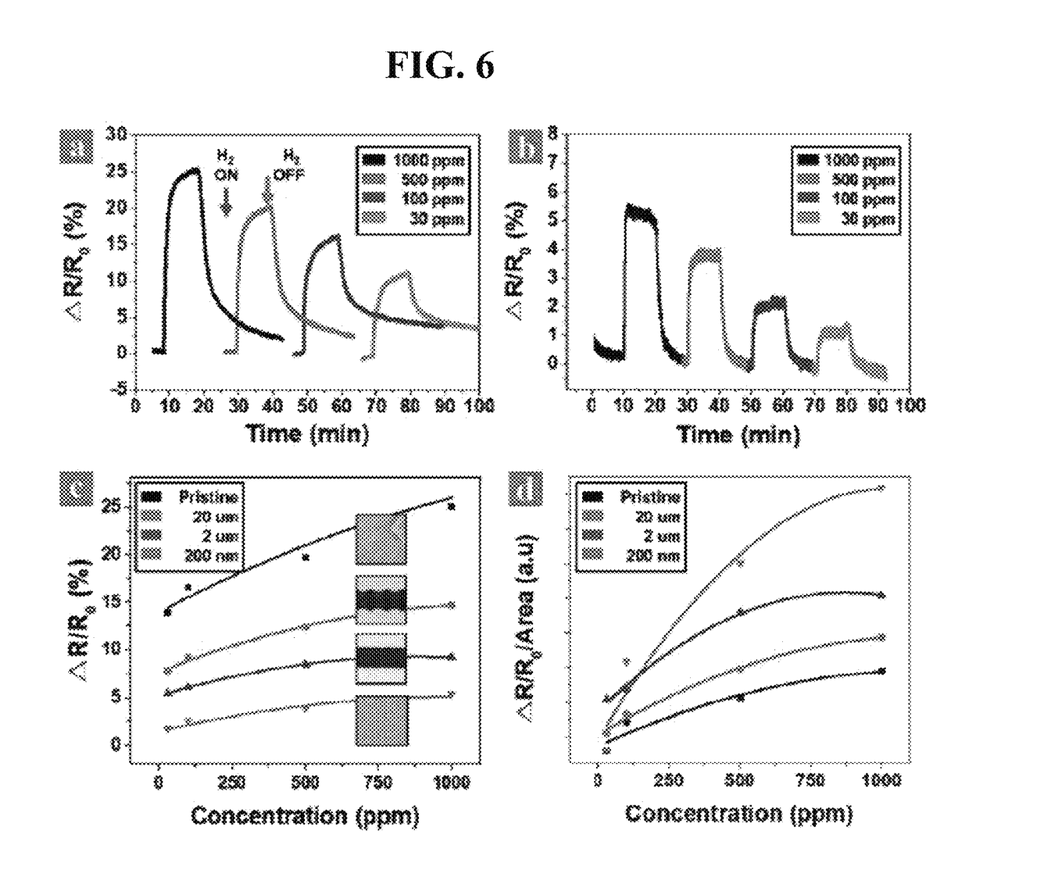
FIG. 6 is graphs depicting resistance changes as a function of time for sensors of Example 2 and Comparative Example 2.

FIG. 6a (Comparative Example 2) and FIG. 6b (Example 2) are graphs depicting results obtained by measuring a resistance change rate of a sensor as a function of time while alternately performing the supply and shut-off of hydrogen, FIG. 6c is a graph showing results obtained by measuring a resistance change rate of a sensor as a function of concentration according to pattern width, and FIG. 6d is a graph showing results obtained by measuring a resistance change rate per unit area of a sensor as a function of concentration according to pattern width.

Referring to FIG. 6a and FIG. 6b, it can be seen that Example 2 has a higher resistance increase rate upon hydrogen supply and a higher resistance recovery rate upon hydrogen shut-off than Comparative Example 2.

Referring to FIG. 6c and FIG. 6d, it can be seen that Example 2 has a higher resistance change rate per unit area with increasing concentration than Comparative Example 2.

Although the present invention has been described with reference to some embodiments, it should be understood that the foregoing embodiments are provided for illustration only and are not to be construed in any way as limiting the present invention, and that various modifications, changes, alterations, and equivalent embodiments can be made by those skilled in the art without departing from the spirit and scope of the invention.

LIST OF REFERENCE NUMERALS

10: substrate
20: graphene
30: chromium layer
40: resist layer

What is claimed is:

1. A method of preparing graphene nanoribbons, comprising:
    forming a chromium layer on a graphene layer;
    forming a resist layer on the chromium layer;
    patterning the resist layer to form a resist pattern;
    patterning the chromium layer to form a chromium pattern; and
    forming a graphene pattern using the chromium pattern as a mask, or the resist pattern and the chromium pattern as a mask.

2. The method of preparing graphene nanoribbons according to claim 1, wherein forming the graphene pattern comprises:
    forming the chromium pattern using the resist pattern as a mask; and
    etching the graphene layer using the chromium pattern as a mask.

3. The method of preparing graphene nanoribbons according to claim 1, wherein patterning the chromium layer to form the chromium pattern comprises:
    etching the chromium layer using the resist pattern as a mask.

4. The method of preparing graphene nanoribbons according to claim 1, wherein patterning the resist layer to form the resist pattern comprises:
    etching the resist layer using laser interference lithography.

5. The method of preparing graphene nanoribbons according to claim 3, wherein etching the chromium layer comprises wet etching.

6. The method of preparing graphene nanoribbons according to claim 3, wherein forming the graphene pattern comprises:
    removing the resist pattern;
    after removing the resist pattern, etching the graphene layer using the chromium pattern as a mask; and
    removing the chromium pattern.

7. The method of preparing graphene nanoribbons according to claim 1, wherein each of the chromium pattern and the graphene pattern has a width of 100 nm to 200 nm.

8. The method of preparing graphene nanoribbons according to claim 1, wherein the chromium pattern has a thickness of 10 nm to 20 nm.

9. A sensor comprising graphene nanoribbons prepared by the method of preparing graphene nanoribbons according to claim 1.

10. The sensor according to claim 9, comprising:
    a catalyst layer and electrodes sequentially formed on the graphene nanoribbons.

11. The sensor according to claim 9, wherein the catalyst layer comprises palladium or platinum.

* * * * *